United States Patent

Wolff et al.

[11] Patent Number: 4,617,255
[45] Date of Patent: Oct. 14, 1986

[54] COLOR COUPLER-CONTAINING PHOTOGRAPHIC MATERIAL

[75] Inventors: Erich Wolff, Solingen; Hans Langen, Bonn; Rudolf Braden, Odenthal, all of Fed. Rep. of Germany

[73] Assignee: Agfa Gevaert Aktiengesellschaft, Leverkusen, Fed. Rep. of Germany

[21] Appl. No.: 798,911

[22] Filed: Nov. 18, 1985

[30] Foreign Application Priority Data

Nov. 30, 1984 [DE] Fed. Rep. of Germany ....... 3443700

[51] Int. Cl.$^4$ .............................................. G03C 1/40
[52] U.S. Cl. ..................................... 430/553; 430/552
[58] Field of Search ................................ 430/552, 553

[56] References Cited

U.S. PATENT DOCUMENTS 4,444,872 4/1984 Kato et al. ........................ 430/553
4,551,422 11/1985 Kimura et al. ..................... 430/553
4,554,244 11/1985 Sato et al. ........................... 430/553

Primary Examiner—Richard L. Schilling
Attorney, Agent, or Firm—Connolly and Hutz

[57] ABSTRACT

Cyan couplers of the formula:

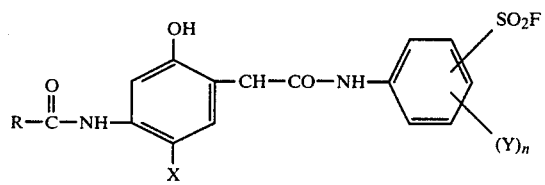

wherein
R = a ballast group
X = H or a leaving group which may be separated during color coupling
Y = halogen, alkyl, alkoxy, aryl or alkylthio
n = 0 to 2 (if n = 2, the radicals Y may be the same or different)

have good dark fading stability of the coupled dye, moreover low secondary color densities and a sufficiently long-wave absorption maximum which is density-independent, furthermore they have high coupling activity and good solubility in high-boiling solvents.

2 Claims, No Drawings

COLOR COUPLER-CONTAINING PHOTOGRAPHIC MATERIAL

This invention relates to a colour photographic material containing new emulsified phenolic cyan couplers having a phenyl ureide structure.

It is known to produce colour photographic images by chromogen development, that is by development of image-wise exposed silver halide emulsion layers in the presence of suitable colour couplers by means of suitable colour-forming developing agents, so-called colour developers, whereby the oxidation product of the developing agents, corresponding to the silver image, reacts with the colour coupler forming a dye image. Aromatic, primary amino group-containing compounds, particularly those of the p-phenylene diamine type are commonly used as colour developers. A number of requirements are generally placed on the colour couplers, as well as on the dyes resulting therefrom following chromogen development. Thus, the coupling speed of the colour couplers with the oxidation product of the colour developer should be as great as possible. The colour couplers, as well as the dyes obtained therefrom, should be sufficiently stable against light, elevated temperature and humidity. This applies both to fresh material and to processed material. For example, the remaining couplers still present in the image white of the processed material should not yellow. Moreover, the dyes should be sufficiently stable against gaseous reducing or oxidizing agents. They must, moreover, be diffusion-fast in the image layer and should be deposited during chromogen development as as fine a grain as possible. The mechanical properties of the layers should not be adversely affected by the colour couplers. Furthermore, the dyes resulting from the colour couplers during the chromogen development must have a favourable absorption curve with a maximum which corresponds to the colour of the partial image desired in each case, and secondary adsorptions which are as low as possible. Thus, a cyan dye should ideally almost completely absorb red light and allow green and blue light substantially to pass through. Moreover, the absorption maxima of the dyes both in colour reversal and colour negative films, should correspond as far as possible to the sensitizing maxima of the colour paper materials used for copying.

Compounds derived from phenol or α-naphthol are generally used as cyan couplers, that is as colour couplers which are suitable for the production of the cyan partial image. Naphtholic cyan couplers have a very bad dark fading behaviour, that is the cyan partial image formed during development bleaches to a comparatively great extent on prolonged storage or in less time at elevated temperature, and reddening of the copy or a density-dependent tinge results.

U.S. Pat. No. 2,772,162 and U.S. Pat. No. 2,369,929 show that cyan couplers having a 2,5-diacylaminophenol structure behave substantially better in this respect. However, such couplers suffer from the disadvantage that the cyan dyes formed therefrom absorb at a shorter wave length by from 20 to 50 nm compared with the above-mentioned naphtholic couplers and consequently do not adapt to the conventional long wave red sensitization of the copying paper.

No. DE-B-1,163,144 shows that by introducing a ureide radical in the 2-position of the aromatic system, couplers result which supply stable azomethine dyes. No. GB-A-1,111,554 shows that the short wave absorption can be shifted to the longer wave area by suitable substitution in the phenyl ureide moiety.

Couplers according to No. EP-A-28 099 having a p-cyano substituent, as well as couplers according to Nos. EP-A-67 689, 73 145, 73 146 and 84 100 absorb at too short a wave length by from 10 to 20 nm, compared with the azomethine dyes of the naphtholic couplers used, which is not ideal for the negative-positive-operating copying process for the above reasons. The constancy of the absorption maximun of the dye developed from the coupler according to the density, leaves a lot to be desired. In order to remedy this disadvantage, the combination of phenolic cyan couplers and non-colour coupling diffusion-stable phenol compounds are described in No. EP-A-116 428. However, even these combinations cannot remove the above-described dependency of $\lambda_{max}$ and density in a satisfactory manner.

Moreover, the coupling speeds of the known couplers are relatively low. On the other hand, it is desirable to use fast couplers for achieving a fine colour grain, particularly in the highly sensitive partial layers. A further disadvantage of the known couplers is additional yellowing in the non-coupled image portion.

An object of the present invention is to provide cyan couplers which have good dark fading stability of the coupled dye, in particular result in as little increase as possible in the yellow fog, moreover have a sufficiently long wave absorption maximum which is density-independent, as well as low secondary densities and which furthermore have a high coupling activity and dissolve well in high-boiling solvents.

This object is achieved by a light-sensitive colour photographic recording material having at least one silver halide emulsion layer and, associated therewith, a non-diffusing phenolic cyan coupler having a 2-phenyl ureide group, characterised in that the cyan coupler corresponds to the following formula I:

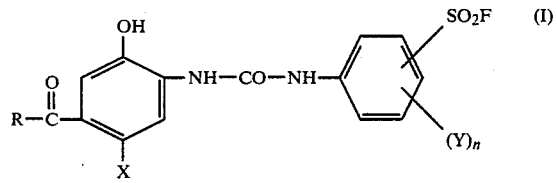

wherein:
X=H or a separable leaving group, for example Cl, —OCH$_2$CH$_2$SO$_2$CH$_3$ or —OCH$_2$CONHCH$_2$CH$_2$OCH$_3$;
Y=halogen, for example Cl, Br or F, alkyl, for example methyl or trifluoromethyl, alkoxy, for example methoxy or ethoxy, aryl or alkylthio;
n=0 to 2, (if n=2, the radicals Y may be the same or different);
R=a ballast group preferably having the structural formula II:

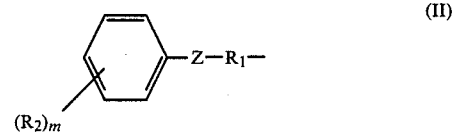

wherein:

Z=O or S;

$R_1$ = an alkylidene group having from 2 to 20 carbon atoms of the formula

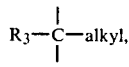

wherein $R_3$ represents H or alkyl;

$R_2$ = hydroxy, carboxy, alkyl, cycloalkyl, aryl, aralkyl, alkoxy, aryloxy, alkylsulphamoyl, arylsulphamoyl, alkylsulphonamido, arylsulphonamido, alkylsulphonyl, arylsulphonyl, alkoxycarbonyl or acyloxy wherein alkyl contains from 1 to 20 carbon atoms, wherein aryl contains from 6 to 20 carbon atoms and wherein alkyl, aryl and aralkyl may also be substituted, if desired, by hydroxy, carboxy, alkoxycarbonyl or acyloxy;

m = 1 to 3;

R may also be a unit of a polymer structure, which is obtained by polymerisation of a monomeric coupler of the formula:

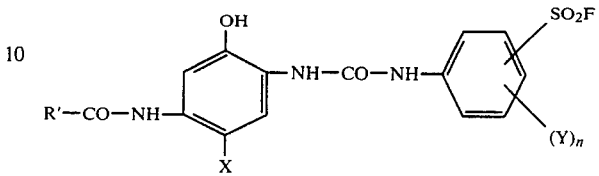

wherein R' contains a polymerisable ethylenically-unsaturated group.

Examples of cyan couplers according to the invention are given below.

| Coupler No. | |
|---|---|
| 1. | 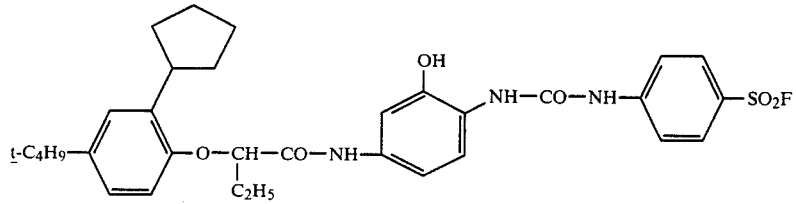 |
| 2. | 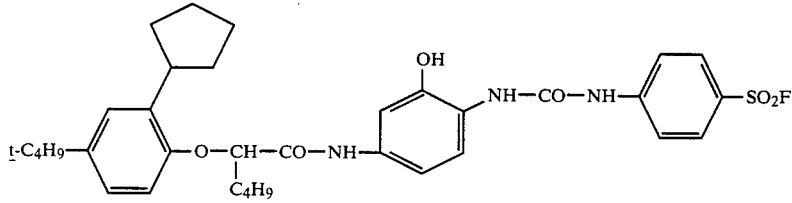 |
| 3. | 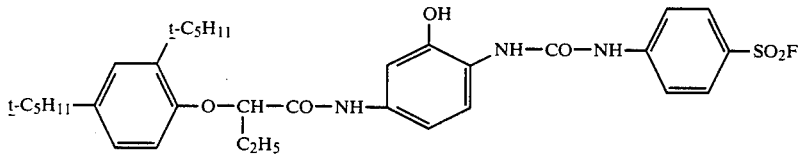 |
| 4. | 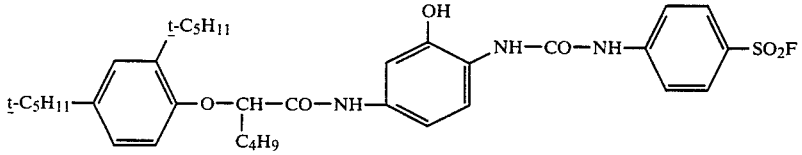 |
| 5. | 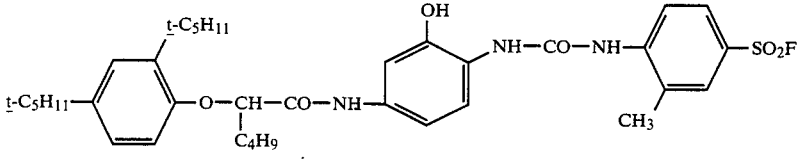 |
| 6. | 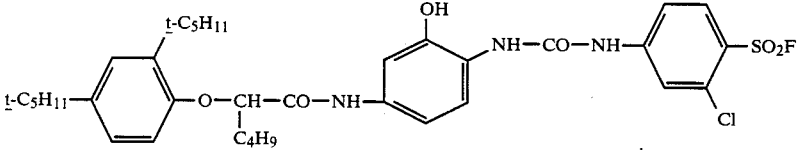 |

| Coupler No. | |
|---|---|
| 7. | 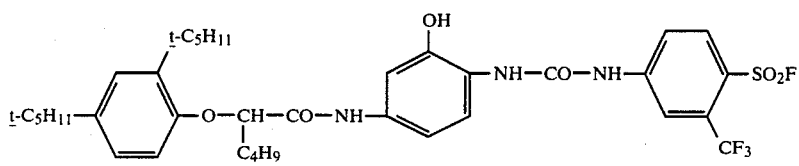 |
| 8. | 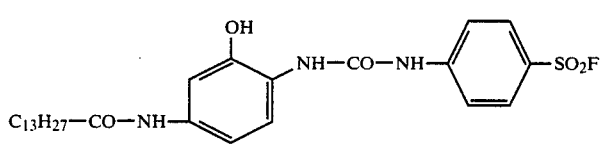 |
| 9. | 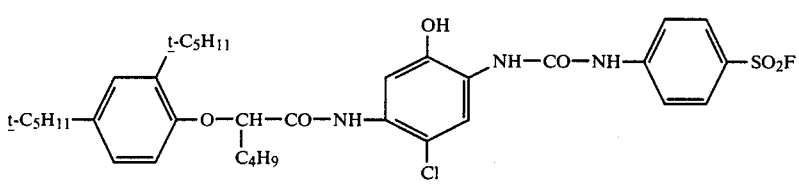 |
| 10. | 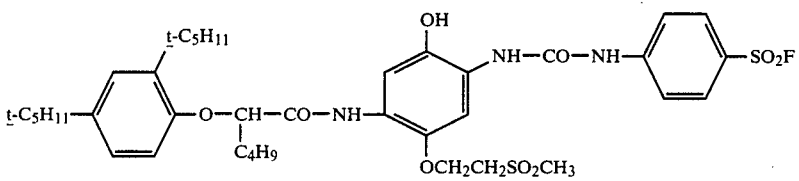 |
| 11. | 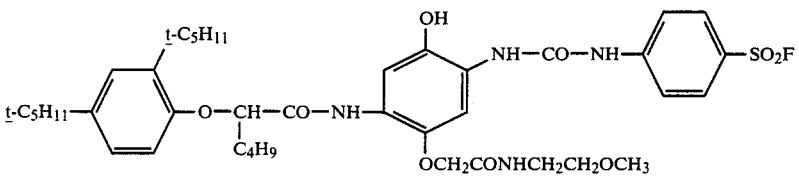 |
The couplers according to the invention may be synthetized by the following methods.
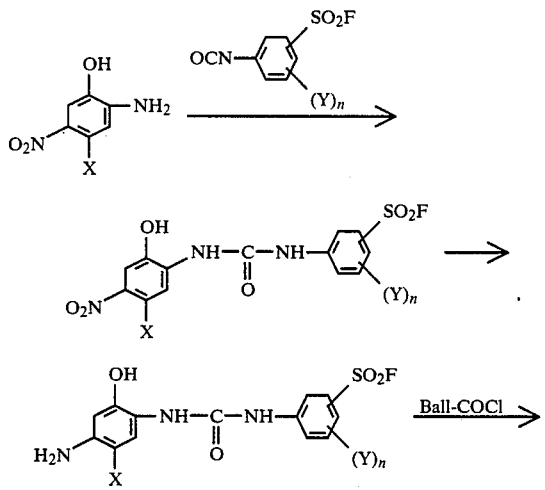
(a)
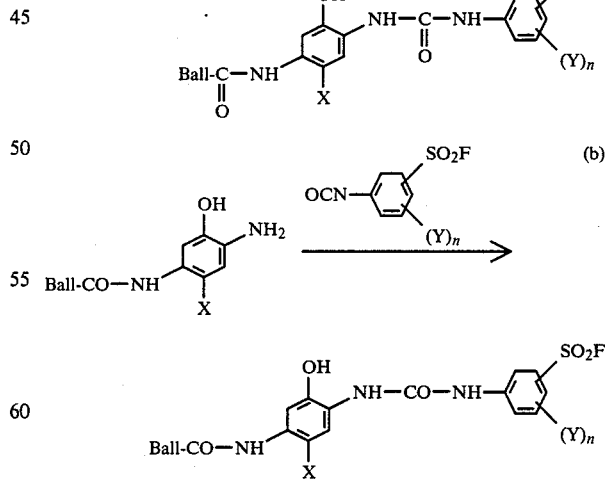
(b)
"Ball" here represents a ballast group.
The production of the couplers according to the invention is described below for compound 4 by the method (b).

PRODUCTION OF COUPLER 4

35 g of 2-amino-5-(2', 4'-di-t-pentyl-phenoxy)hexanoylamino-phenol hydrochloride are dissolved in 250 ml of ether, and treated with 10 g of potassium carbonate and 15 g 4-isocyanato-phenylsulphonic acid fluoride.

Subsequent stirring is carried for 1 hour at room temperature, then precipitation takes place in ice/water and the precipitate drawn off by suction and dried is recrystallized from ether/petroleum ether.

Yield: 20 g.

Melting point: 160° C.

Titration with tetrabutyl ammonium hydroxide in dimethyl sulphoxide indicates a content of 99.8%.

The couplers 1, 3, 5 and 8 according to the invention are produced in corresponding manner.

The compounds according to the invention provide valuable colour couplers which result during chromogen development in cyan dyes having excellent stability properties. They are outstandingly suitable for use in light-sensitive silver halide emulsion layers of photographic single or multilayer materials. The cyan couplers, however, need not necessarily be incorporated in the light-sensitive layers; rather, it is also possible to accommodate them in a binder layer which is adjacent to a light-sensitive silver halide emulsion layer.

The cyan couplers according to the invention can be incorporated, according to known methods, in the silver halide emulsion or in another binder mixture. Since the couplers according to the invention are so-called emulsifying couplers, that is hydrophobic compounds, the incorporation takes place in known manner by dissolving in suitable organic solvents, for example in esters, aliphatic carboxylic acids, particularly in ethyl acetate or methylene chloride, and emulsifying this solution in the silver halide emulsion ready for casting. This method may optionally be modified by the simultaneous use of oily coupler solvents. This process is known from U.S. Pat. No. 2,304,940 and U.S. Pat. No. 2,322,027. The couplers according to the invention are characterised by good solubility in high-boiling solvents, such as tricresyl phosphate, dibutyl phthalate, diethyl lauramide etc. This results in good storage stability and digestion stability of the emulsifiers used for the coating, as a result of low crystallization.

Emulsions of silver halides, such as silver chloride, silver bromide or mixtures thereof, possibly with a low content of silver iodide of up to 10 mol %, are suitable as light-sensitive emulsions in one of the hydrophilic binders used in conventional manner, such as protein, particularly gelatine, polyvinyl alcohol, polyvinyl pyrrolidone, cellulose derivatives, such as carboxyalkyl cellulose, particularly carboxymethyl cellulose, or derivaties of alginic acid.

The emulsions may also be chemically sensitized, for example by addition of sulphur-containing compounds during chemical ripening, for example allylisothiocyanate, allylthiourea, sodium thiosulphate and the like. Moreover, reducing agents, for example the tin compounds described in Belgian Pat. Nos. 493,464 or 568,687, furthermore polyamides, such as diethylene triamine, or aminomethane sulphinic acid derivatives, for example according to Belgian Pat. No. 547,323, may also be used as chemical sensitizers.

Noble metals or noble metal compounds, such as gold, platinum, palladium, iridium, rhenium or rhodium, are also suitable as chemical sensitizers. This method of chemical sensitization is described in the article by R. Koslowsky, Z. Wiss. Phot. 46, 65–72, (1951).

Moreover, it is possible to sensitize the emulsions using polyalkylene oxide derivatives, for example polyethylene oxide having a molecular weight of from 1000 to 20,000, also using condensation products of alkylene oxides and aliphatic alcohols, glycols, cyclic dehydration products of hexitols, with alkyl-substituted phenols, aliphatic carboxylic acids, aliphatic amines, aliphatic diamines and amides. The condensation products have a molecular weight of at least 700, preferably greater than 1000. To achieve particular effects, these sensitizers may naturally be used in combination, as described in Belgian Pat. No. 537,278 and in British Pat. No. 727,982.

The colour coupler-containing emulsions may moreover contain spectral sensitizers, for example the conventional mono- or poly-methine dyes, such as cyanines, hemicyanines, streptocyanines, merocyanines, oxonols. Hemioxonols, stryryl dyes or others, also tri- or multi-nuclear methine dyes, for example rhodacyanines or neocyanines. Such sensitizers are described, for example, in the work by F. M. Hamer "The Cyanine Dyes and Related Compounds", (1964) Interscience Publishers John Wiley and Sons. The colour couplers according to the invention are preferably used, however, in those emulsions which are sensitized for red light.

The emulsions may contain the conventional stabilizers, such as homopolar or salt-like compounds of mercury with aromatic or heterocyclic rings, such as mercaptotriazoles, simple mercury salts, sulphonium mercury double salts and other mercury compounds. Azaindenes, preferably tetra-or penta-azaindenes, are moreover suitable as stabilizers, particularly those which are substituted by a hydroxyl or amino group. Such compounds are described in the article by Birr, Z. Wiss. Phot. 47 2–27 (1952). Further suitable stabilizers are, inter alia, heterocyclic mercapto compounds, for example phenylmercaptotetrazole, quaternary benzthiazole derivatives, benztriazole and the like.

For the production of a photographic emulsion layer, one or more couplers of the given formula may moreover be used together with one or more known couplers, for example with masking or DIR couplers.

The emulsions may be hardened in conventional manner, for example using formaldehyde or halogen-substituted aldehydes, which contain a carboxyl group, such as mucobromic acid, diketones, methane sulphonic acid esters, dialdehydes and the like.

For producing the cyan partial image, the conventional colour developers are used, for example the conventional aromatics, at least one primary amino group-contianing compounds of the p-phenylene diamine type.

Usable colour developers are, for example, N,N-dimethyl-p-phenylene diamine, N,N-diethyl-p-phenylene diamine, monomethyl-p-phenylene diamine, 2-amino-5-diethylamino-toluene, N-butyl-N-ω-sulphobutyl-p-phenylene diamine, 2-amino-5-(N-ethyl-N-β-methane sulphonamidoethyl-amino)-toluene and the like. Further usable colour developers are described, for example, in J. Amer. Chem. Soc. 73, 3100 to 3125 (1951).

The advantages of the couplers according to the invention are shown by the following experiments.

EXAMPLE 1

Determination of the coupling kinetics

The coupling kinetics are determined as keff according to the method described in U.S. Pat. No. 4,315,070 and No. DE-A-2,853,362. For this purpose the couplers are emulsified according to the general procedure described below.

100 g of colour coupler are dissolved in a mixture of 80 g of dibutyl phthalate and 300 ml of ethyl acetate with heating to 50° C. and immediately stirred into 1 kg of an 8% gelatine solution heated to 50° C. and mixed with 50 ml of a 10% solution of the Na-salt of di-sec.-naphthalene sulphonic acid, by means of a high-speed mixing siren of the type MS 1 (Kotthoff GmbH, Cologne). The ethyl acetate is then evaporated in a vacuum and the dispersion is solidified at 6° C. and stored.

The kinetics values obtained can be seen in Table 1.

The couplers 1,4 and 6 according to the invention have a substantially higher keff value than the comparative couplers A, B and C of the prior art.

1. A less sensitive layer haivng a red-sensitized silver bromide iodide emulsion (6 mol % of $I^\theta$) of 2.9 g of $AgNO_3$ and 1.5 g of gelatine with 0.45 g of cyan coupler incorporated therein.

2. A more sensitive layer having a red-sensitized silver bromide iodide emulsion (8 mol % of $I^\theta$) of 3.5 g of $AgNO_3$ and 2.2 g of gelatine having 0.2 g of cyan coupler incorporated therein (the same compound as in layer 1.)

3. A 0.8 g gelatine-containing intermediate layer.

4. A hardening protective layer of 0.3 g of gelatine, over which 0.4 g of a water-soluble carbamoyl pyridinium salt is introduced as hardening agent.

The dispersion of the cyan couplers was made as described in Example 1.

In each case two samples of the material are exposed behind a graduated neutral wedge and processed according to the processing method described in Ernest Ch. Gehret, British Journal of Photography 1974, p. 597, the first sample is immediately evaluated after processing, the second, however, only after a 4-week long

TABLE 1

| Coupler No. | keff $\frac{1}{mol \cdot sec}$ |
| --- | --- |
| 1 | 6,000 |
| 4 | 5,700 |
| 6 | 5,800 |
| A | 3,500 |
| B | 890 |
| C | 3,400 |

Coupler A:

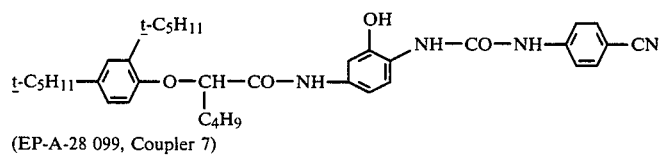

(EP-A-28 099, Coupler 7)

Coupler B:

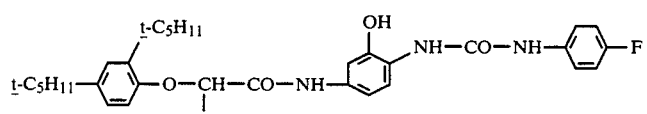

(according to Research Disclosure 24734)

Coupler C:

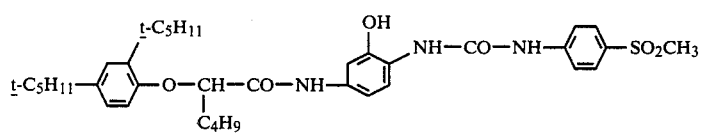

(EP-A-84 100, Coupler 4)

EXAMPLE 2

The following layers are successively applied on a transparent emulsion support provided with an antihalation layer. The quantity data relate in each case to 1 m². For the silver halide applicaiton, the quantities are given as g of $AgNO_3/m^2$.

storage at 80° C. and 40% relative humidity. The absorption maxima are measured at D=0.5 and D=2.0, as well as the extent of the yellow fog. It may be clearly seen from Table 2 that the couplers according to the invention have a $\lambda_{max}$ which is density-independent compared with the known couplers, this even applies in comparison with a naphtholic cyan coupler of the structure D, and that the degree of yellowing of the developed material is lower.

TABLE 2

| | λmax (fresh) nm | | Dark fading stability after storage (4 weeks/80° C./40% relative humidity) | |
| --- | --- | --- | --- | --- |
| Coupler No. | D = 0.5 | D = 2.0 | density reduction (%) | increase in yellow fog |
| 4 | 698 | 698 | 4 | 0.13 |
| A | 685 | 687 | 4 | 0.18 |
| C | 681 | 690 | 4 | 0.17 |

TABLE 2-continued

| | | | | |
|---|---|---|---|---|
| D | 690 | 700 | 57 | 0.14 |
| E | 678 | 684 | 7 | 0.17 |

Coupler D:

[Structure: 1-hydroxy-2-naphthamide with –CO–NH–(CH$_2$)$_4$–O–phenyl(cyclopentyl)(C$_4$H$_9$)]

(DE-C-22 14 060, coupler 6)

Coupler E:

[Structure: t-C$_5$H$_{11}$, t-C$_5$H$_{11}$ substituted phenyl–O–CH(C$_4$H$_9$)–CO–NH–phenyl(OH)–NH–CO–NH–phenyl–SO$_2$N(CH$_3$)$_2$]

(corresponds to EP-A-67 689, Example 81)

We claim:

1. Light-sensitive colour photographic recording material having at least one silver halide emulsion layer and, associated therewith, a non-diffusing phenolic cyan-coupler having a 2-phenylureide group, characterised in that the cyan coupler has the following formula:

[Structure showing phenol with R–CO–NH– substituent, X substituent, and –NH–CO–NH–phenyl with SO$_2$F and (Y)$_n$ substituents]

wherein:
R = a ballast group;
X = H or a leaving group which may be separated during colour coupling;
Y = halogen, alkyl, alkoxy, aryl or alkylthio;
n = 0–2; if n = 2, the radicals Y may be the same or different.

2. Light-sensitive colour photographic recording material according to claim 1, characterised in that the ballast group R has the following formula:

[Structure: phenyl with (R$_2$)$_m$ substituents and –Z–R$_1$–]

wherein:
Z = O or S;
R$_1$ = an alkylidene group having from 2 to 20 carbon atoms of the formula $$R_3-\overset{|}{\underset{|}{C}}-alkyl,$$

wherein R$_3$ represents H or alkyl;
R$_2$ = hydroxy, carboxyl, alkyl, cycloalkyl, aryl, aralkyl, alkoxy, aryloxy, alkylsulphamoyl, arylsulphamoyl, alkylsulphoamido, arylsulphonamido, alkylsulphonyl, arylsulphonyl, alkoxycarbonyl or acyloxy, wherein alkyl contains from 1 to 20 carbon atoms, wherein aryl contains from 6 to 20 carbon atoms, and wherein alkyl, aryl and aralkyl may also be substituted, as desired, by hydroxy, carboxy, alkoxycarbonyl or acyloxy;
m = 1 to 3.

* * * * *